(12) United States Patent
Rosenberg

(10) Patent No.: US 9,726,639 B1
(45) Date of Patent: Aug. 8, 2017

(54) APPARATUS FOR DETECTING MAGNETIC FLUX LEAKAGE AND METHODS OF MAKING AND USING SAME

(71) Applicant: Jeffrey S. Rosenberg, Broken Arrow, OK (US)

(72) Inventor: Jeffrey S. Rosenberg, Broken Arrow, OK (US)

(*) Notice: Subject to any disclaimer, the term of this patent is extended or adjusted under 35 U.S.C. 154(b) by 98 days.

(21) Appl. No.: 14/599,893

(22) Filed: Jan. 19, 2015

Related U.S. Application Data

(60) Provisional application No. 61/928,849, filed on Jan. 17, 2014.

(51) Int. Cl.
*G01N 27/82* (2006.01)
*G01P 15/00* (2006.01)
*G01K 13/00* (2006.01)

(52) U.S. Cl.
CPC ............. *G01N 27/82* (2013.01); *G01K 13/00* (2013.01); *G01P 15/00* (2013.01)

(58) Field of Classification Search
CPC ........ G01N 27/82; G01N 27/83; G01N 27/87; G01N 27/72; G01N 27/80; G01N 27/9046; G01N 27/023; G01N 27/9033; G01B 7/105; G01B 7/107; G01V 3/101; G01K 13/00; G01P 15/00
See application file for complete search history.

(56) References Cited

U.S. PATENT DOCUMENTS

| | | | | |
|---|---|---|---|---|
| 4,602,212 A * | 7/1986 | Hiroshima | ......... | G01N 27/9046 324/227 |
| 5,130,652 A * | 7/1992 | Kawakami | ........... | G01N 27/902 324/238 |
| 6,057,684 A * | 5/2000 | Murakami | ............. | G01N 27/82 324/225 |
| 6,587,048 B1 * | 7/2003 | Bomya | ............... | B60R 21/0136 180/274 |
| 8,046,160 B2 * | 10/2011 | Carter | ...................... | A47F 10/04 340/539.13 |
| 8,970,212 B2 * | 3/2015 | Kurokawa | ............. | G01N 27/90 324/239 |
| 2004/0261547 A1 * | 12/2004 | Russell | ..................... | F17D 5/00 73/865.8 |
| 2005/0007108 A1 * | 1/2005 | Dogaru | ................ | G01N 27/904 324/235 |
| 2012/0109565 A1 * | 5/2012 | Tsukada | ................. | G01N 27/83 702/106 |
| 2013/0221950 A1 * | 8/2013 | Lanter | ....................... | G01L 1/12 324/207.2 |
| 2013/0264926 A1 * | 10/2013 | Zhao | .................. | A47B 88/0414 312/319.8 |

* cited by examiner

*Primary Examiner* — Julian Huffman
*Assistant Examiner* — Michael Konczal
(74) *Attorney, Agent, or Firm* — Hall Estill Law Firm

(57) ABSTRACT

An apparatus and method for detecting magnetic flux leakage in an object. The apparatus includes a frame assembly, a sensor bar and a U shaped magnetic circuit consisting of first and second magnet and steel pieces 44, 46 and 42 connecting the magnets. The sensor bar is connected to the frame assembly and includes a plurality of coils and at least one sensor operatively connected to at least one of the plurality of coils. The first magnet and the second magnets are connected steel pieces and to the frame assembly. They form a U shaped magnetic circuit which is completed by the steel plate being inspected. The sensor bar is placed between the tips of the U shaped magnetic circuit.

6 Claims, 4 Drawing Sheets

APPARATUS FOR DETECTING MAGNETIC FLUX LEAKAGE AND METHODS OF MAKING AND USING SAME

CROSS-REFERENCE TO RELATED APPLICATIONS

The present application claims benefit under 35 U.S.C. §119(e) of U.S. Provisional Application Ser. No. 61/928,849, filed Jan. 17, 2014, which is hereby expressly incorporated herein by reference in its entirety.

BACKGROUND

Magnetic flux leakage (MFL) is a magnetic method of testing that is used to detect corrosion, erosion and pitting in steel structures, such as pipelines and storage tanks. A u-shaped magnetic circuit is used to magnetize the steel. The magnetic field "leaks" from the steel at areas where there is corrosion or missing metal. In an MFL device, a magnetic field sensor is placed between the poles of the magnetic circuit to detect the leakage field.

MFL inspection devices have been used for many years with only coils, or coil pairs, as sensors. Wire coils sense changes in magnetic field (AC component). Coils are useful, in that, the interface uses simple low-power electronics, they can be very sensitive, they are somewhat temperature stable, they sense fields inside the coil so a single coil can cover a large area, mechanically rugged, and multiple sensors can be manufactured to be very similar. However, coils only respond to changes in magnetic fields, and the size of the output signal is related to the size of the magnetic field, number of coil turns and the rate of change of the magnetic field (Faradays Law).

More recently, MFL inspection devices have used magnetoresistors (e.g., Hall effect devices), rather than coils. Magnetoresistive sensors sense absolute magnetic field levels (DC component). Magnetoresistors respond to steady state and changing magnetic fields. However, magnetoresistors interface needs are somewhat complex electronics, multiple sensors are all different and need individual calibration, sensor output changes with temperature and mechanical stress, are not sensitive to tiny magnetic fields, and require power to operate.

The inspection tools are used to find metal loss flaws for things like: railroad rails, pipelines, spherical liquid natural gas (LNG) tanks and above-ground storage tank floors and walls and the like. For example, typically, the floor of a storage tank is made by welding rectangular steel plates together. The floor is sometimes coated with fiberglass or a tar-like substance. The MFL inspection device rides over a bumpy surface on the tank floor. Most of the time, the bumps cause false signals to be seen by the magnetic field sensors. When there are many bumps, it is hard to see the signals from metal loss flaws. The operator of the MFL inspection device has to move the device back and forth over a short distance that doesn't have any bumps to see if the signal is from the flaw.

To this end, although MFL devices exist, there is a need for an improved MFL detection apparatus with improved accuracy, repeatibility and one that filters out false signals. It is to such an MFL detection apparatus and methods of making and using such apparatus and components of the apparatus that the present disclosure is directed.

BRIEF DESCRIPTION OF THE DRAWING(S)

DETAILED DESCRIPTION

The present disclosure relates generally to a MFL detection apparatus/scanner, and more particularly, but not by way of limitation, to an improved MFL detection apparatus and methods for making and using same. One embodiment of this disclosure is directed to sensor systems that are more accurate than previous systems, are better able to filter out false signals, and are easier to calibrate. The multi-sensor approach measures the MFL signals along with the signal environment. Various embodiment(s) of this disclosure combines a unique group of sensors to accurately measure MFL.

Figure 1:
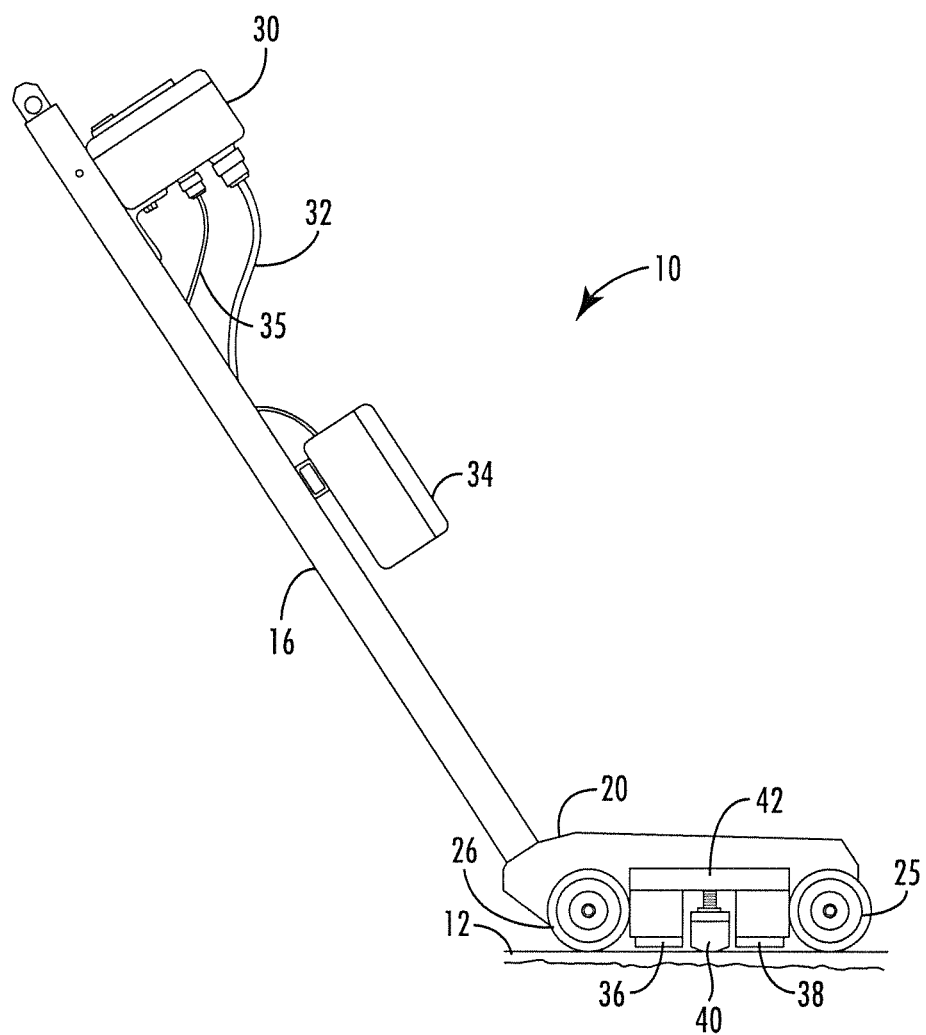
FIG. 1 is a side view of an apparatus for detecting magnetic flux leakage constructed in accordance with one embodiment of the present disclosure, the apparatus being positioned on a steel plate.
Figure 2:
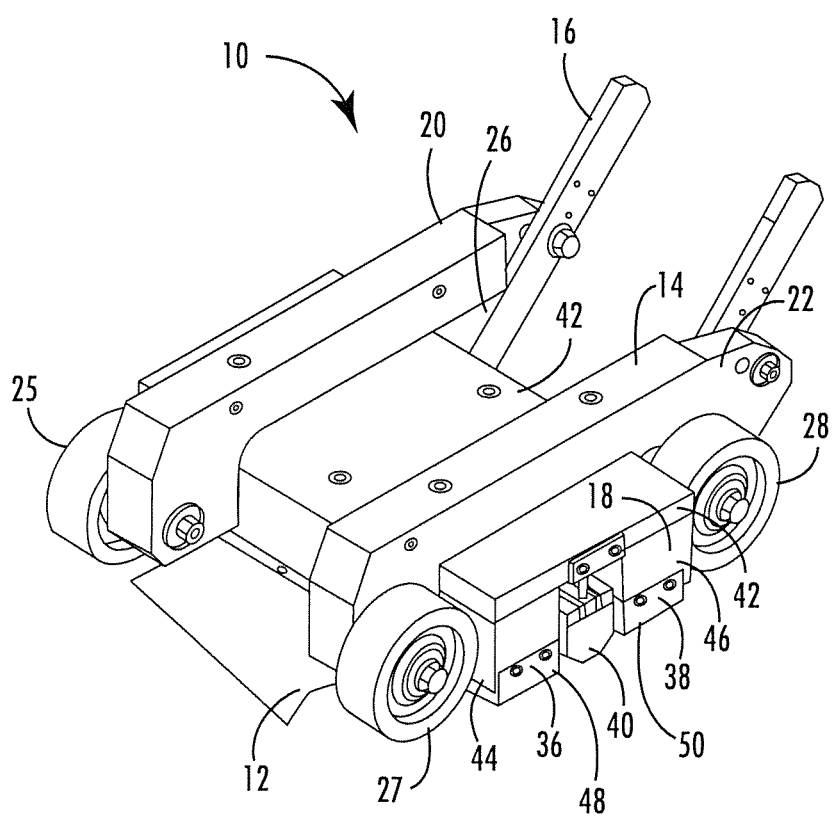
FIG. 2 is a perspective view of the apparatus of FIG. 1.

Referring now to the drawings, and more particularly to FIGS. 1 and 2, one embodiment of an apparatus for detecting magnetic flux leakage 10 is shown positioned over a portion of a steel plate 12 of an above ground storage tank. It should be understood that although the apparatus 10 disclosed herein is discussed in use on the steel floor of an above-ground storage tank, the apparatus 10, as disclosed herein, may be utilized for detecting flaws in railroad rails, pipelines, LNG tanks, walls, and the like. Further, it should be understood by one of ordinary skill in the art that the apparatus 10 may be used on any magnetizable material.

Broadly, the apparatus 10 includes a frame assembly 14, a handle assembly 16 and a magnetic flux assembly 18 which supports instrumentation for performing the magnetic flux leakage measurements. The frame assembly 14 includes a pair of spatially disposed substantially u-shaped members 20 and 22. The frame assembly 14 is mounted on a plurality of wheels 25, 26, 27 and 28 so that the apparatus 10 may be movable over the steel plate 12 being inspected.

The handle assembly 16 is connected to the u-shaped members 20 and 22 of the frame assembly and is configured for an operator to steer and manipulate the apparatus 10 over the surface of the steel plate 12. A computer and command module 30 is mounted on the handle assembly 16 for controlling the electronic and/or other powered operation of the apparatus 10. The module 30 is provided with a display screen (not shown) for displaying detection/inspection results and instructions for communicating with the operator. Further, module 30 stores and transmits the magnetic flux leakage detection information via a signal path 32 from the magnetic flux assembly 18. Once magnetic flux leakage is detected, the information will reflect on the module 30. The signal path can be either manual signal paths, or electronic communication signal paths. The electronic communication signal paths can be logical and/or physical links between various software and/or hardware utilized to implement the present invention. The physical links could be air-way or cable communication links. When the apparatus is implemented, the signal paths may not be separate signal paths but may be a single signal path or multiple signal paths. In addition, it should be understood that the various information does not always have to flow between the components of the present invention in the exact manner shown provided the information is generated and received to accomplish the purposes set forth herein.

A power source 34, such as a battery, is shown for providing power to the apparatus 10 by way of a cable 35. The power source 34 is positioned on the handle assembly 16. However, it will be understood by one of ordinary skill in the art that the power source may be positioned any place on the apparatus 10 and power may be provided to the apparatus in various ways. Further, any known power source used for providing power to an object can be utilized herein, so long as the power source functions in accordance with the present disclosure.

The magnetic flux assembly 18 includes a pair of magnet assemblies 36 and 38 and a sensor bar 40. The pair of magnet assemblies 36 and 38 and sensor bar 40 are operably connected to a steel support member 42 positioned in and operably connected to the u-shaped members 20 and 22 of the frame assembly 14. Each of the magnet assemblies 36 and 38 are positioned on opposite sides of the sensor bar 40. Each of the magnet assemblies 36 and 38 are provided with a steel portion 44 and 46, respectively, and a magnet portion 48 and 50, respectively. The steel portions 44 and 46 are operably connected to the steel support member 42 and the magnet portion 48 and 50 are operably connected to the steel portions 44 and 46, respectively. This forms a magnetic circuit that is completed when sitting on the steel plate 12.

Figure 3:
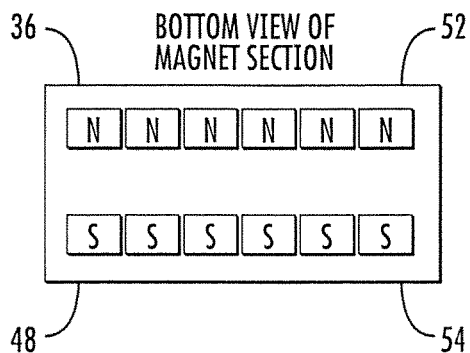
FIG. 3 is a bottom view of one embodiment of a magnet portion of the magnetic flux assembly of the apparatus of FIG. 1 constructed in accordance with the present disclosure.

Referring to FIG. 3, each magnet portion 48 and 50 (not shown) are configured to provide two rows of permanent magnets forming rows of north and south pole faces 52 and 54, respectively. When the pole faces of the magnets are magnetically coupled to the steel plate 12, a continuous magnetic circuit is formed. In one preferred embodiment, Neodymium iron boron magnets produced by K&J Magnetics, Inc. may be utilized (2"×2"×½", Nickel plated N42 material). However, it should be understood that any size or type of magnet may be utilized in the apparatus 10 so long as the magnet functions in accordance with the present disclosure.

Figure 4:
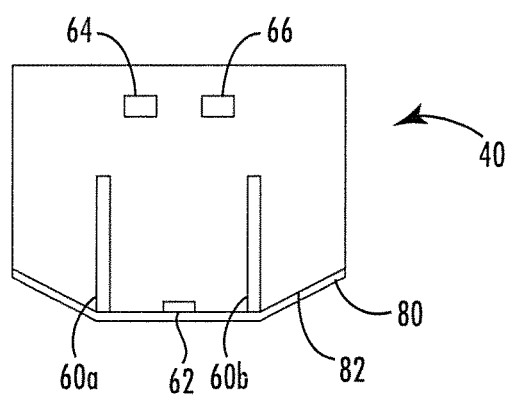
FIG. 4 is a cross-sectional view of a sensor bar of the apparatus of FIG. 1 constructed in accordance with one embodiment of the present disclosure.
Figure 5:
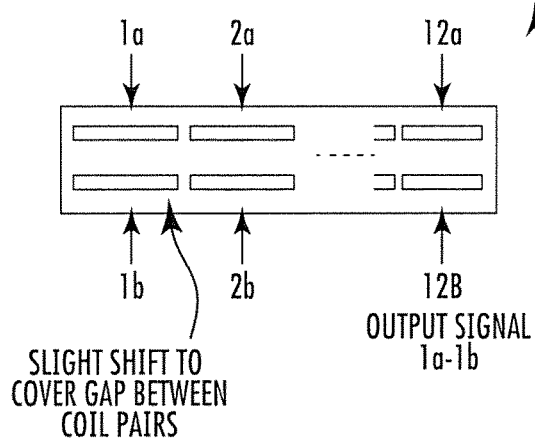
FIG. 5 is a top cross-sectional view of one embodiment of an array pattern of a pair of coils of the sensor bar of FIG. 4.

Referring to FIGS. 1-2 and 4, the sensor bar 40 includes a pair of coils 60 (60a and 60b), a plurality of magnetic field sensors (magnetoresistor) 62, a temperature sensor 64, and an accelerometer 66. In one embodiment, the coils 60 are arranged perpendicular to the steel plate 12 being inspected to measure the tangential magnetic field changes and the magnetic field sensors 62 are arranged parallel to the steel plate 12 being inspected to measure the normal component of the magnetic field. There are a plurality of coil pairs and sensors positioned and/or stacked end to end along the length of the sensor bar 40 to examine a wide area of the steel plate 12. The length of the sensor bar 40 may vary and thus the number of coils pairs and magnetic field sensors will vary. Referring to FIG. 5, by way of example, the coils 60 are shown in twelve pairs of one inch coils (1A-12A and 1B-12B) that can inspect twelve inches of the steel plate at one time. As shown, there is a slight shift between the coils so as to cover any gap between the coil pairs. If the coil pairs are not shifted, there is a small gap between coil pairs that is not sensitive to magnetic field changes. Thus, when one of the coils in a pair is shifted there is no area that is not sensitive to magnetic field changes.

Figure 6:
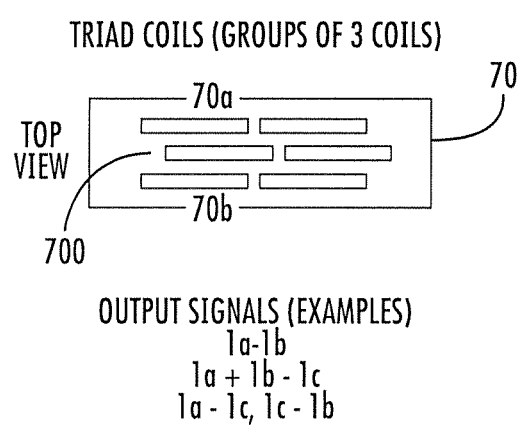
FIG. 6 is a top cross-sectional view of another embodiment of an array pattern of a triad of coils of the sensor bar of FIG. 4.

Referring to FIG. 6, in another embodiment, the pair of coils 60 may be provide in group of three coils 70 (70a, 70b, 70c) in a triad configuration. The triad configuration consists of three coils 70 perpendicular to the steel plate to be inspected. The center coil 70c has twice as many windings as the two outer coils 70a and 70b. The coils 70 are wired to subtract the outer coils 70a and 70c from the central coil 70c. The output of the triad coil 70 is sent into an amplifier (not shown). The arrangement of the triad coil 70 makes it sensitive to MFL "flaw shaped" signals and not sensitive to background noise. A single pair of coils effectively subtracts common mode noise (noise induced in both coils). A typical MFL flaw signal from sensor coils rises to a peak above a reference line, then falls below the reference line and finally returns to the reference line. The triad configuration has two sets of coils wired to look for the point where the flaw signal goes from positive to negative (that is the center of a flaw). Two signals from each coil pair in the triad configuration could also be made and let the computer make better flaw decision with the extra flaw signal data.

Referring back to FIG. 4, the temperature sensor 64 is positioned in the sensor bar 40 and helps to compensate the sensor and magnet variations related to temperature. Various temperature sensors may be utilized in apparatus 10, for example, in one preferred embodiment, analog devices ADT7301, 13 bit±1° C. digital temperature sensor are used.

The accelerometer 66 is positioned in the sensor bar 40 and used to compensate the output of the coils 60 and 70 since the output varies with speed. Most MFL systems attempt to get a constant velocity so they do not have to compensate for changes in velocity. The accelerometer 66 also communicates to the module 30 when the apparatus 10 is sensing, sitting still, or being transported so battery power 34 can be maximized. One example of an accelerometer that may be utilized in the apparatus 10 are analog devices ADXL 362, 3 axis±2g MEMS accelerometer. Although shown positioned in the sensor bar 40, in another embodiment, the accelerometer may be positioned in the module 30. It should be understood that the accelerometer may be positioned at various locations on the apparatus 10, so long as the accelerometer functions in accordance with the present disclosure as described herein.

A thin non-magnetic stainless steel wear surface portion 80 is provided on a bottom surface 82 of the sensor bar 40 so as to engage the surface of the steel plate 12 (FIGS. 1 and 2) and protect the coils 60 and magnetic field sensors 62.

The apparatus 10 reduces sensor outputs that are not related to metal loss flaws (false calls), gives a better size indication of the metal loss flaw by compensating for temperature, instrument speed and distance between the metal being inspected and the sensor assembly, and saves battery power by knowing when the apparatus 10 is being used as a sensor.

The construction and arrangement of the apparatus 10, as shown in the various exemplary embodiments, is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, and elements shown as multiple parts may be constructed to be integrally formed, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present embodiments.

From the above description, it is clear that the present disclosure is well adapted to carry out the objects and to attain the advantages mentioned herein as well as those inherent in the invention. While embodiments of the invention have been described for purposes of this disclosure, it will be understood that numerous changes may be made which will readily suggest themselves to those skilled in the art and which are accomplished within the spirit of the invention disclosed.

What is claimed is:

1. An apparatus for detecting magnetic flux leakage in a metal object, comprising:
    a plurality of magnets operatively connected to a portion of the apparatus such that the plurality of magnets create a magnetic field when the plurality of magnets are positioned so as to magnetize the metal object;
    a plurality of coils positioned between the plurality of magnets wherein the plurality of coils provides a signal for measuring changes in the magnetic field strength; and
    at least one sensor positioned between the plurality of magnets and operatively connected to at least one of the plurality of coils wherein the at least one sensor measure the absolute strength of the magnetic field so that the signal from the plurality of coils and the signal from the at least one sensor generate a magnetic flux leakage output signal which represents the amount of metal loss in the metal object.

2. The apparatus of claim 1, wherein the plurality of coils are in pairs.

3. The apparatus of claim 1, wherein the plurality of coils are in groups of three.

4. The apparatus of claim 1, wherein the at least one sensor is a plurality of magnetic field sensors.

5. The apparatus of claim 1, wherein the at least one sensor is a temperature sensor for improving the magnetic flux leakage output signal.

6. The apparatus of claim 1, wherein the at least one sensor measures speed and direction for improving the magnetic flux leakage output signal.

* * * * *